US012605479B1

(12) United States Patent　　　(10) Patent No.:　US 12,605,479 B1

Cowan-Richardson　　　　　　　(45) Date of Patent:　Apr. 21, 2026

(54) PORTABLE SHOE SOLE DECONTAMINATION DEVICE WITH OPTIONAL INTERNAL SHOE DISINFECTANT AND DEODORIZER

(71) Applicant: Nakiesha Cowan-Richardson, Hanscom AFB, MA (US)

(72) Inventor: Nakiesha Cowan-Richardson, Hanscom AFB, MA (US)

(73) Assignee: Nakiesha Cowan-Richardson, McDonough, GA (US)

( * ) Notice: Subject to any disclaimer, the term of this patent is extended or adjusted under 35 U.S.C. 154(b) by 1004 days.

(21) Appl. No.: 17/404,992

(22) Filed: Aug. 17, 2021

Related U.S. Application Data

(60) Provisional application No. 63/067,245, filed on Aug. 18, 2020.

(51) Int. Cl.
A61L 2/24　　　(2006.01)
A61L 2/10　　　(2006.01)

(52) U.S. Cl.
CPC ..................................... A61L 2/24 (2013.01); A61L 2/10 (2013.01); *A61L 2202/11* (2013.01); *A61L 2202/121* (2013.01); *A61L 2202/122* (2013.01); *A61L 2202/14* (2013.01); *A61L 2202/16* (2013.01)

(58) Field of Classification Search
CPC .......... A61L 2/24; A61L 2/10; A61L 2202/11; A61L 2202/121; A61L 2202/122; A61L 2202/14; A61L 2202/16
See application file for complete search history.

(56) References Cited

U.S. PATENT DOCUMENTS

| | | | | |
|---|---|---|---|---|
| 5,863,497 | A * | 1/1999 | Dirksing | A61B 90/80 134/1 |
| 10,765,769 | B2 * | 9/2020 | Eidman | A61L 2/10 |
| 2009/0314308 | A1 * | 12/2009 | Kim | A61L 2/0088 134/1 |
| 2013/0101461 | A1 * | 4/2013 | Gil | A61L 2/10 250/455.11 |
| 2013/0336839 | A1 * | 12/2013 | Gil | A61L 2/10 422/107 |
| 2018/0207302 | A1 * | 7/2018 | Vasilenko | A61N 5/0624 |
| 2021/0153470 | A1 * | 5/2021 | Yoo | A63B 22/02 |
| 2021/0330830 | A1 * | 10/2021 | Zerello | A61L 2/10 |
| 2022/0001062 | A1 * | 1/2022 | Le | A61L 9/20 |
| 2022/0249718 | A1 * | 8/2022 | Rifkin | A47L 13/16 |
| 2023/0055756 | A1 * | 2/2023 | Brown | A61L 2/10 |
| 2023/0293742 | A1 * | 9/2023 | Kocinski | A61L 2/10 422/3 |

FOREIGN PATENT DOCUMENTS

FR　　　2792208　A1 *　10/2000　...........　A43D 3/1491

OTHER PUBLICATIONS

English translation of FR2792208 (Year: 2000).*

* cited by examiner

*Primary Examiner* — Regina M Yoo

(57)　　　　ABSTRACT

A portable, rechargeable battery-powered sanitizing device for decontaminating shoe soles may be provided. The device may include a housing enclosure with an access door, a divider within the housing enclosure forming two shoe chambers, and UV-C LED lights directed upward from the bottom of each shoe chamber. The device may also include proximity sensors located among and in communication with the UV-C LED lights, The proximity sensors may detect whether a shoe sole is present above it and illuminated the UV-C LED lights with shoe soles above to sterilize the shoe soles.

11 Claims, 9 Drawing Sheets

PORTABLE SHOE SOLE DECONTAMINATION DEVICE WITH OPTIONAL INTERNAL SHOE DISINFECTANT AND DEODORIZER

CROSS REFERENCE TO RELATED APPLICATIONS

This application is a non-provisional application which claims a benefit of priority to U.S. Provisional Application No. 63/067,245, filed Aug. 18, 2020, which is hereby incorporated herein by reference in its entirety.

FIELD

The disclosure relates to portable device for deactivating pathogens on shoe soles. Particularly, the present disclosure relates to a transportable, rechargeable battery-powered (via USB or other interface hardware) device that utilizes ultraviolet UV-C light to disinfect shoe soles by considerably neutralizing pathogens found on the bottom of shoe soles, with an option to also disinfect and deodorize the inside of the shoe.

BACKGROUND

Pathogens on shoe soles have been a longstanding concern. While maneuvering in public and private settings, shoe soles frequently encounter various pathogens and contaminants. According to the Journal of Applied Microbiology, "shoe soles are possible vectors for infectious diseases," and pathogens were identified on shoe soles in healthcare settings, in the community, and in the animal worker setting (Rashid, VonVille, Hasan, & Garey, 2016, p. 1223). This is a major societal concern, especially in homes with infants or toddlers.

There is a growing approach to disinfecting objects with ultraviolet C ultraviolet radiation ("UV-C" or "UVC"), which utilizes short wavelengths that disrupt the DNA of bacterial and viral cells; thus, deactivating pathogens. Several devices using UV-C light have been developed to address the issue of contaminants and pathogens on shoe soles. Certain devices that utilize UVC light to disinfect shoe soles require individuals to stand in a large, non-portable machine during the process of emitting UVC light to the individual's shoe soles. These devices connect to an external source to generate power to the machine. Thus, the concern of convenience and practicality arises.

Other devices are portable and self-powered but still require individuals to stand on the device during the treatment process, which can pose challenges being well-fitted to the busy, fast-paced life of many. Pediatric emergency physician, Dr. Sabreen Akhter (2020), recounted in the Washington Post the challenges of healthcare providers regarding contamination on shoes being the first thing that is considered. Common recommendations to prevent transferring pathogens on shoe soles to other settings are removing or switching out shoes prior to entering the setting, washing the shoes (Office of Public Affairs, 2015), or using disinfectant wipes to disinfect the shoe soles (Eske, 2020). This suggests the underutilization of the current disinfecting shoe sole devices due to challenges in practicality, convenience, and mere size of the device. Therefore, a need exists in the field to provide a compact, portable and convenient shoe sole disinfecting device to overcome the above-mentioned challenges.

BRIEF DESCRIPTION OF THE FIGURES

The accompanying drawings, which are incorporated in and constitute a part of this disclosure, illustrate various embodiments of the present disclosure. In the drawings.

DEFINITIONS

Figure 1:
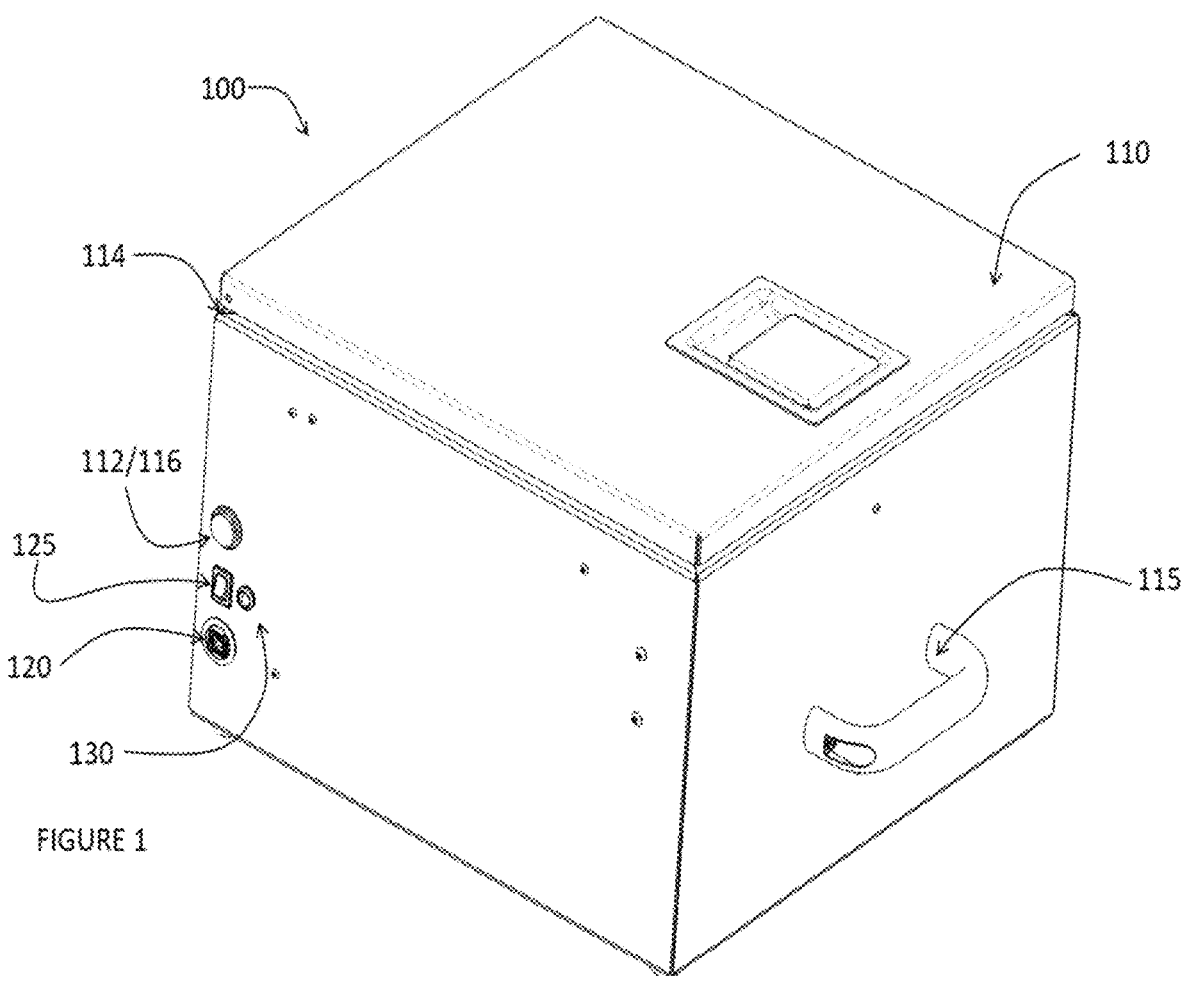
FIG. 1 depicts a perspective view of an embodiment of a portable, internal power-sourced shoe sole sanitizer with its access door in a closed position, illustrating a disinfection activation button, a power switch, a power indicator light, an active disinfection cycle indicator light, and a battery charging port.

The phrase "a" or "an" entity as used herein refers to one or more of that entity.

The terms "optional" or "optionally" as used herein means that a subsequently described element, event, or circumstance may but need not occur, and that the description includes instances where the event or circumstance occurs and instances in which it does not.

References to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, unless otherwise indicated or made clear from the context, the term "or" should generally be understood to mean "and/or" and, similarly, the term "and" should generally be understood to mean "and/or."

Recitation of ranges of values herein are not intended to be limiting, referring instead individually to any and all values falling within the range, unless otherwise indicated herein, and each separate value within such a range is incorporated into the specification as if it were individually recited herein.

The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the embodiments.

In the following description, it is understood that terms such as "first," "second," "third," "upper," "lower," "below," and the like, are words of convenience and are not to be construed as implying a positional or chronological order or otherwise limiting any corresponding element unless expressly stated otherwise.

For the purpose of this disclosure, the center of any component can refer to a two-dimensional or three-dimensional center. The term center may also refer to a center of mass of a given element.

DETAILED DESCRIPTION

Overview

This overview is provided to introduce a selection of concepts in a simplified form that are further described below in the detailed description. This overview is not intended to identify required or essential features of the claimed subject matter. Nor is this overview intended to be used to limit the scope of the claimed subject matter.

The present disclosure relates to a rechargeable (via USB or other hardware interface) battery-powered device that utilizes ultraviolet light with wavelengths between 200-290 nanometers (UV-C), and more particularly with wavelengths between 270-285 nanometers (UV-C), to disinfect (other appropriate words include decontaminate, sanitize, sterilize, clean, neutralize, and deactivate) shoe soles by considerably neutralizing pathogens found on the bottom of shoes. Such UV-C lighting is facilitated by use of UV-C light emitting diode ("LED") lights or other UV-C light sources such as UV Mercury lamps. The present disclosure also includes an option to disinfect and deodorize the inside of the shoe. Disinfecting the shoe soles and the internal shoe is achieved by internally powering UV-C light emission once shoes are placed within an internal housing unit, with the soles facing the light emission of the UV-C light while inserting removable UV-C light shoe racks or wands into the shoes. There is also an option to remove the shoe racks and place the shoes on top of the internal UV-C lighting panel or platform. The sanitizing system can be recharged via a USB port, a charging base, a plugin power outlet, or other hardware interface.

It is a purpose of this disclosure to provide a shoe cleaner (e.g., sanitizer, decontaminator, deactivator, disinfectant, neutralizer, sterilizer) that uses ultraviolet light to sterilize the soles of shoes. The shoe cleaner may include a light proof enclosure with two (light separated) internal chambers, one for each shoe. Also, the device may expose only the soles of the shoes to UV-C light for a predetermined amount of time and then report completion to the user.

Both the foregoing overview and the following example embodiments are examples and explanatory only and should not be considered to restrict the disclosure's scope, as described, and claimed. Further, features and/or variations may be provided in addition to those set forth herein. For example, embodiments of the disclosure may be directed to various feature combinations and sub-combinations described in the example embodiments.

Example Embodiments

The following detailed description refers to the accompanying drawings. Wherever possible, the same reference numbers are used in the drawings and the following description to refer to the same or similar elements. While embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims.

FIG. 1 depicts a perspective view of an embodiment of a portable, internal power-sourced shoe sole sanitizer (sanitizing device) 100 with a housing enclosure 114 including its access door 110 in a closed position. FIG. 1 also depicts a disinfection activation button 112, a power switch 125, a power indicator light 130, an active disinfection cycle indicator light 116 within the button 112, a handle 115, and a battery charging port 120.

Figure 2:
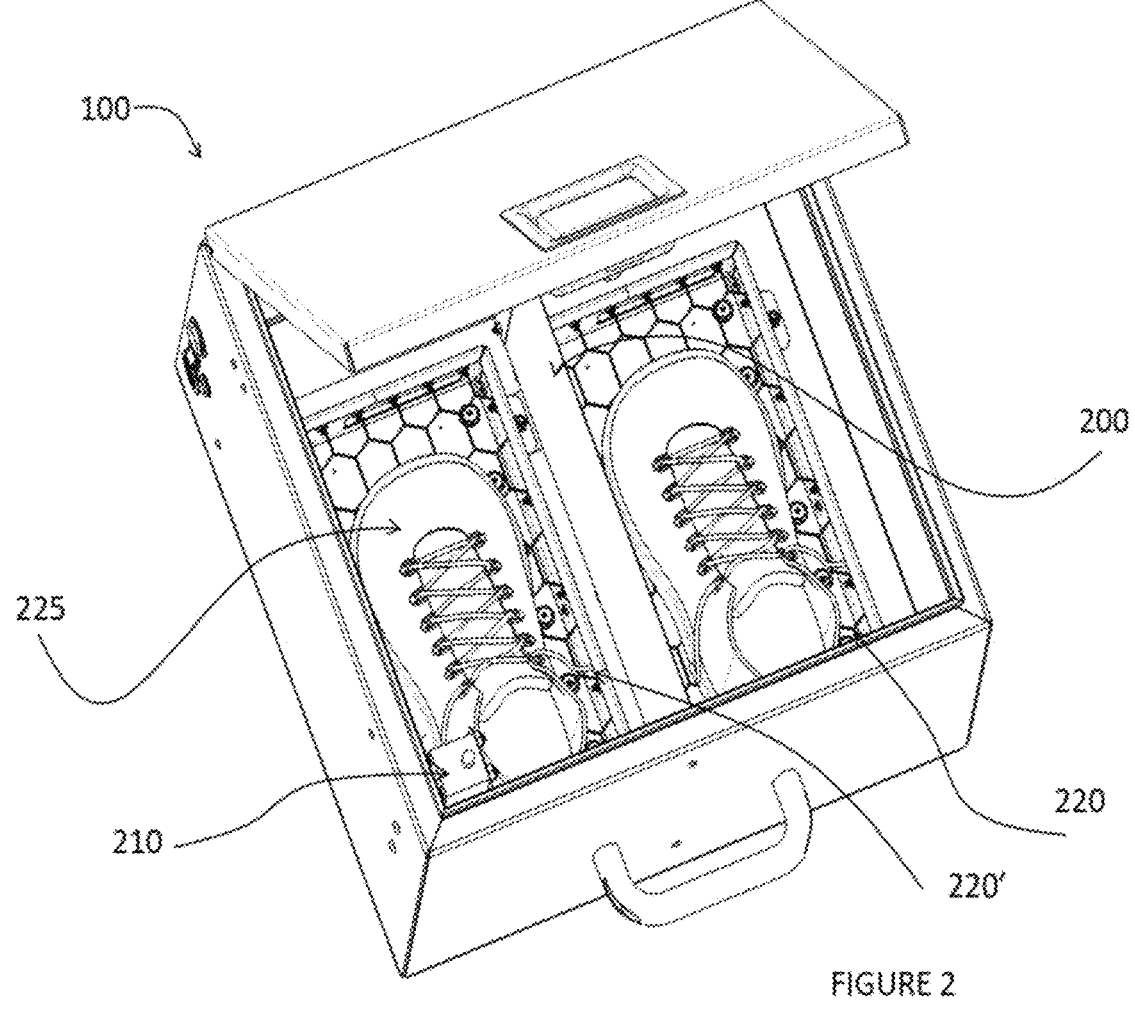
FIG. 2 depicts a perspective view of the shoe sole sanitizer of FIG. 1 with its access door in an open position, a safety switch interlock in communication with the access door, and a divider forming two shoe chambers containing UV-C LED lights, each chamber loaded with a shoe with its sole set on a screen atop UV-C LED lighting panel each screen and UV-C lighting panel forming a UV-C shoe module.

FIG. 2 depicts a perspective view of the shoe sole sanitizer 100 of FIG. 1 with its access door 110 in an open position, a safety switch interlock 210 in communication with the access door 110, and a divider 200 forming two shoe chambers 200,220'. Whenever the access door 110 is not in communication or in contact with the safety switch interlock 210, for safety reasons, the interlock 210 prevents a disinfection cycle from beginning without the access door 210 closed.

Figure 3:
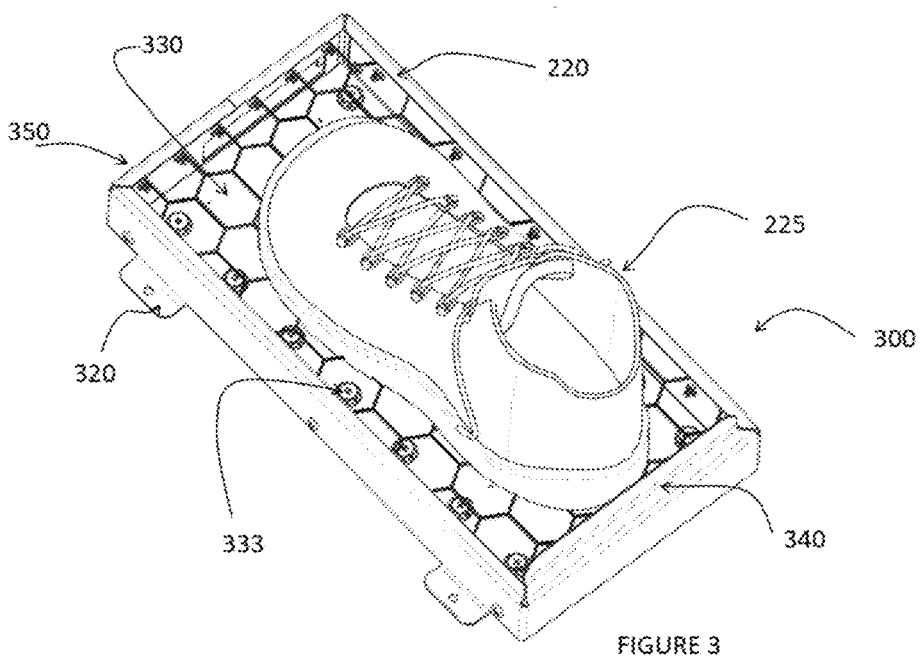
FIG. 3 depicts a perspective view of a UV-C shoe module 300 at the bottom of the shoe chambers of FIG. 2 including a UV-C LED lighting panel with UV-C LED lights, lamps, or bulbs.

FIG. 3 depicts a perspective view of a UV-C shoe module 300 at the bottom of the shoe chambers 220, 220' of FIG. 2 including a UV-C LED lighting panel 320 containing UV-C LED lights, bulbs, or lamps 330 and proximity sensors 333, each chamber 220 loaded with a shoe 225 with its sole set on a screen 357 atop the UV-C LED lighting panel 320 each screen 357, proximity sensors 333, and lighting panel 320 forming a UV-C shoe module 300.

The sanitizer 100 may include a light proof housing enclosure 114 with two (light separated) internal chambers 220 and 220', one for each shoe 225 as shown in FIG. 2. In short, the housing enclosure 114 may be completely without light from outside the housing enclosure 114 when the access door 110 is in the closed position. This ensures that potentially harmful UV-C light does not escape the sanitizing device 100 once the access door 110 is closed.

Each chamber 220 and 220' may work identically. UV-C lighting 330 is located on panels 320 at the bottom of each chamber 220/220', directed upward. The shoe 225 sets on a screen 357, in the chamber 220, above the lighting panel 320. The heel of the shoe 225 is placed on a heel end 340 of the UV-C module 300 and the shoe chamber 220/220'.

Figure 4:
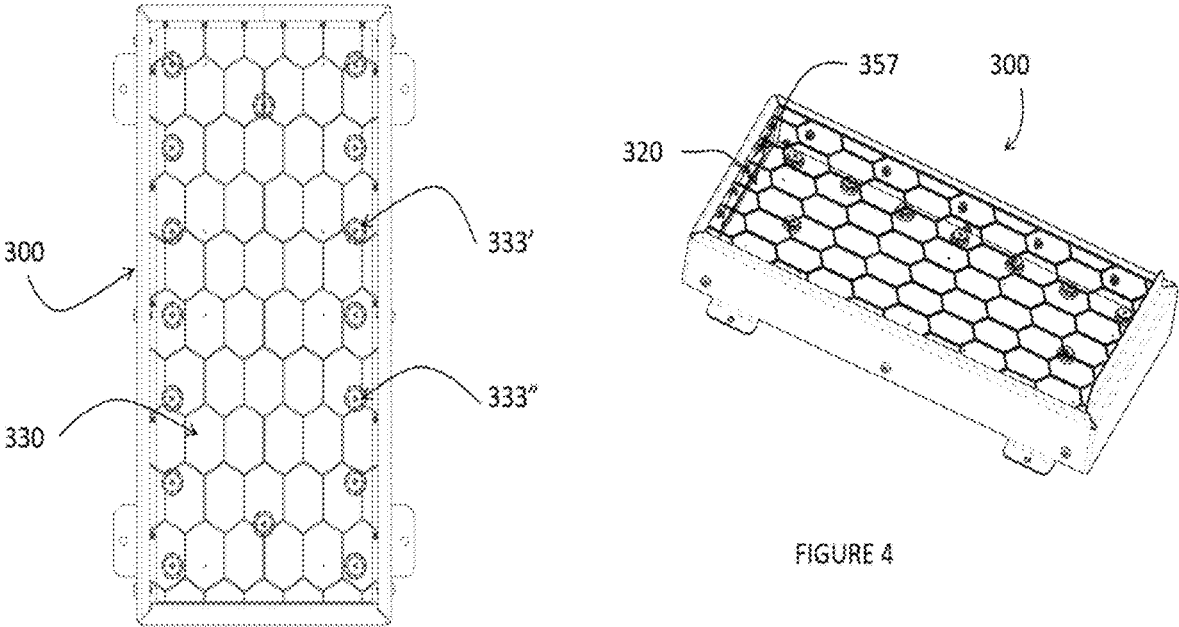
FIG. 4 depicts top view and a perspective view of the UV-C shoe module of FIG. 3, including the UV-C LED lighting panel of FIG. 3 with placement of proximity sensors.

FIG. 4 depicts top view and a perspective view of the UV-C shoe module 300 of FIG. 3, including the UV-C LED lighting panel 320 of FIG. 3 with placement of proximity sensors 333, 333', 333". UV-C LED lights 330 are arranged in side-by-side pairs. These pairs may be located from the heel end of the panel 340 out towards the toe of the shoe 225 (and past) to a toe end 350 of the panel 320 and chamber 220. Proximity sensors 333 may be located, one each, between each pair of UV-C LED lamps 330. A user may be required to close the access door 110 to the housing enclosure 114 (for eye safety) before the sanitizing device 100 can be activated and not shut off by the safety interlock 210. Then, the sanitizing device 100 may be allowed to be activated and UV-C LED lights 330 illuminated by the user.

Upon startup, the proximity sensors 333 on the panel 320 (between the UV-C LED light 330 pairs as shown in FIG. 4) may measure the shoe 225 by sequentially testing each UV-C LED 330 pair lighting position to verify that the sole of the shoe 225 is detected atop and then UV-C LED 330 pairs that are under the sole of the shoe 225 may be illuminated with UV-C light. UV-C LED 330 (pairs) that are not directly under the shoe 225 may not activate. With this disclosed embodiment only the sole of the shoe 225 is directly illuminated, while the top of the shoe 225 is in shadow, preventing UV damage to the top of the shoe.

Additionally, the inside of the housing enclosure 114, and both sides of the divider 200, may be painted with matte black finish, preventing reflected UV light from irradiating the top of the shoe(s) 225. Also, for the same reasons, each of the two shoe chambers may only receive light from within its own shoe chamber when the access door is in the closed position to prevent UV-C light from bleeding over to the adjacent chamber and possibly damaging the top of either shoe 225.

The safety interlock 210 with the access door 110 prevents the UV lighting from staying illuminated if the door 110 to the enclosure 114 is opened during the sterilizing process (for eye safety). After a specific time has passed, illumination is turned off and the soles of the shoes 225 may be fully sterilized. An indicator light 116 on the enclosure 114 notifies the user when the UV sterilization is in progress and when sterilization has completed (See FIG. 1). When the predetermined amount of time is complete the sanitizing device 100 may indicate completion to a user of the sanitizing device 100 by turning off the indicator light 116.

The disinfection cycle indicator light 116 is in electrical communication with the UV-C LED lights 330 and/or a timer such that when the predetermined amount of time is complete the disinfection cycle indicator light 116 turns off along with the UV-C LED lights 330 and when the sanitizing device exposes such shoe sole to at least a portion of the UV-C LED lights the disinfection cycle indicator light 116 turns on.

Figure 5:
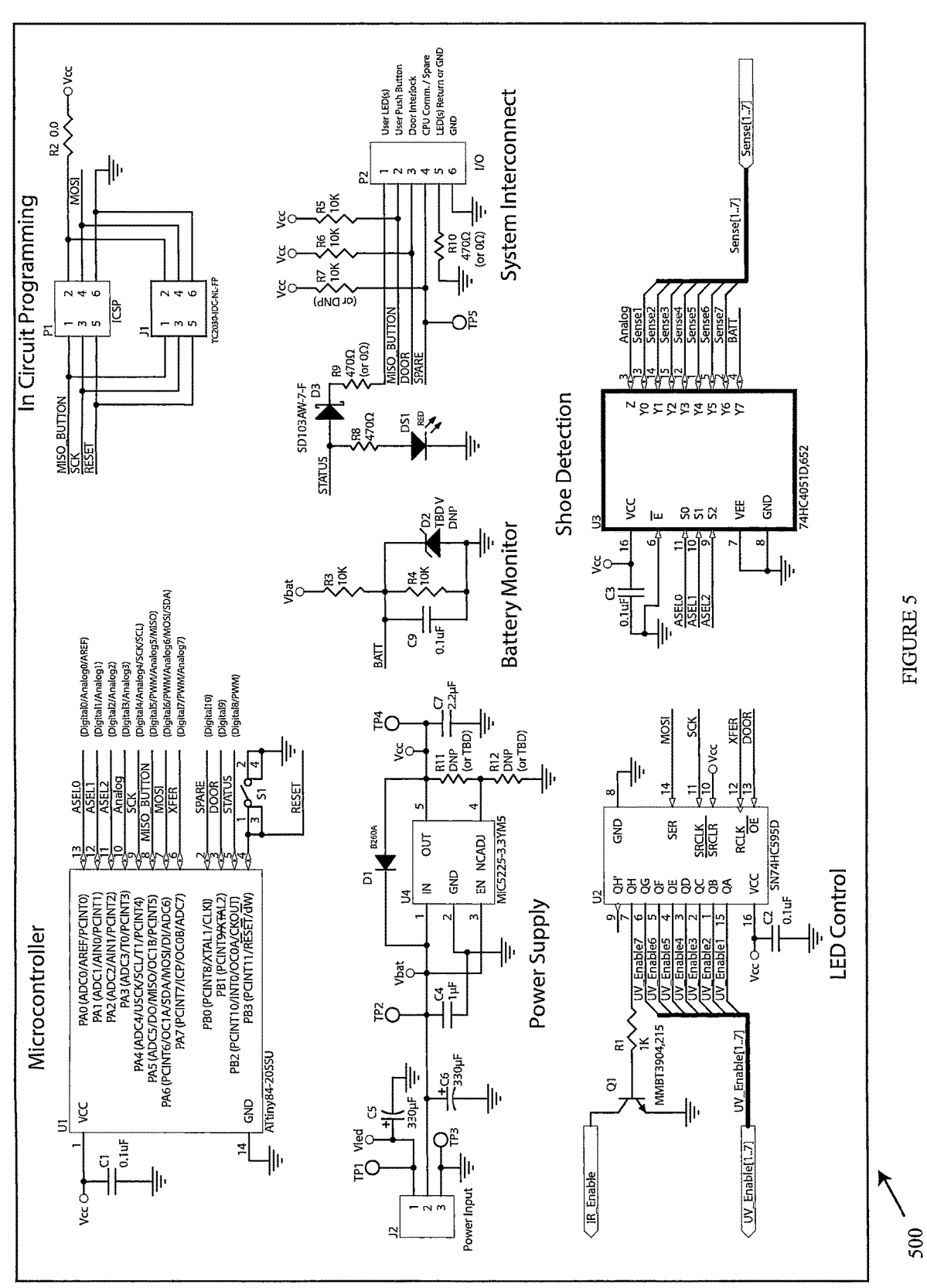
FIG. 5 depicts UV-C controller circuitry schematic for the shoe sole sanitizer of FIG. 1.
Figure 6:
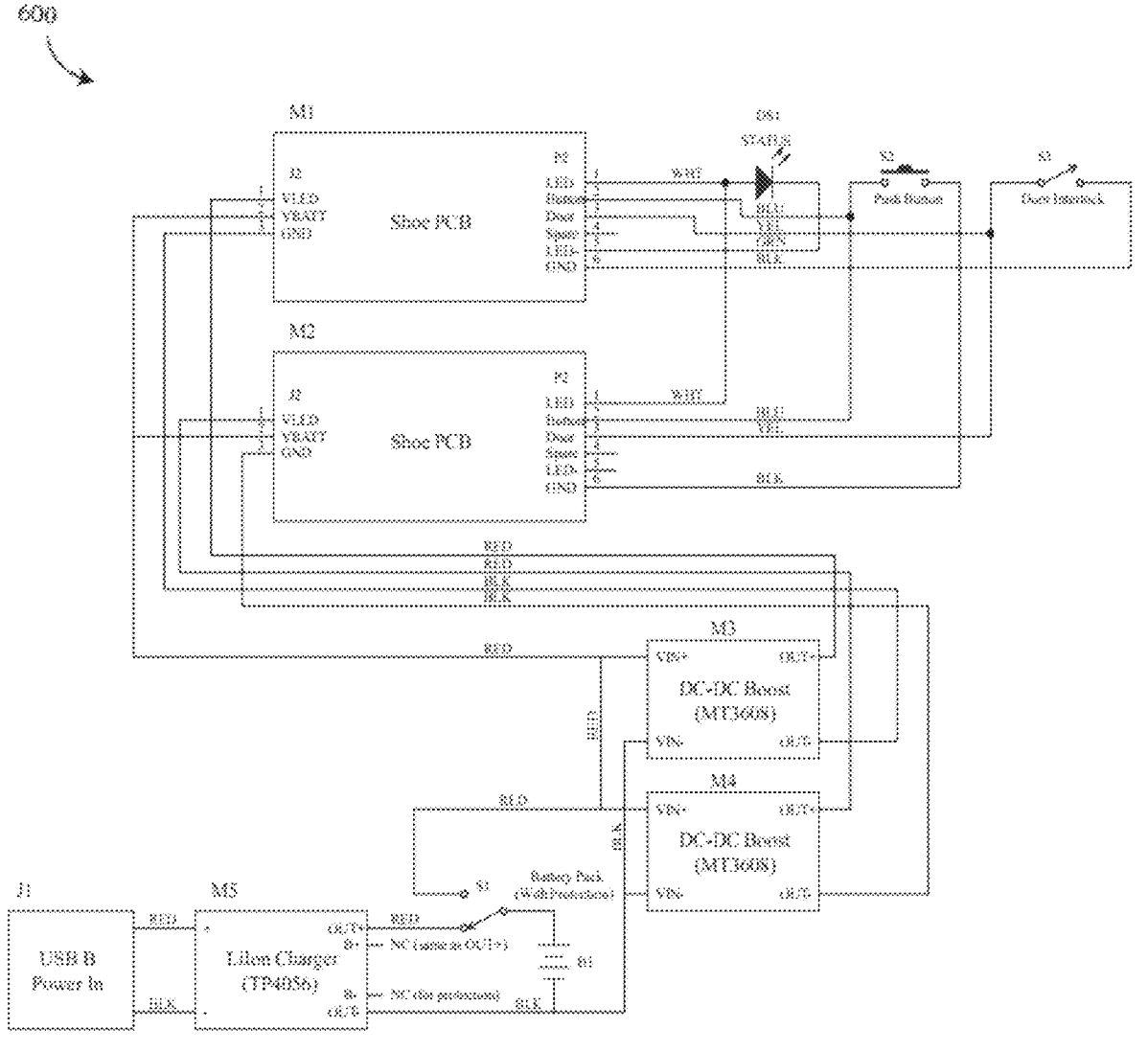
FIG. 6 depicts a circuit wiring diagram for the UV-C shoe sole sanitizer chassis of FIG. 1.
Figure 7:
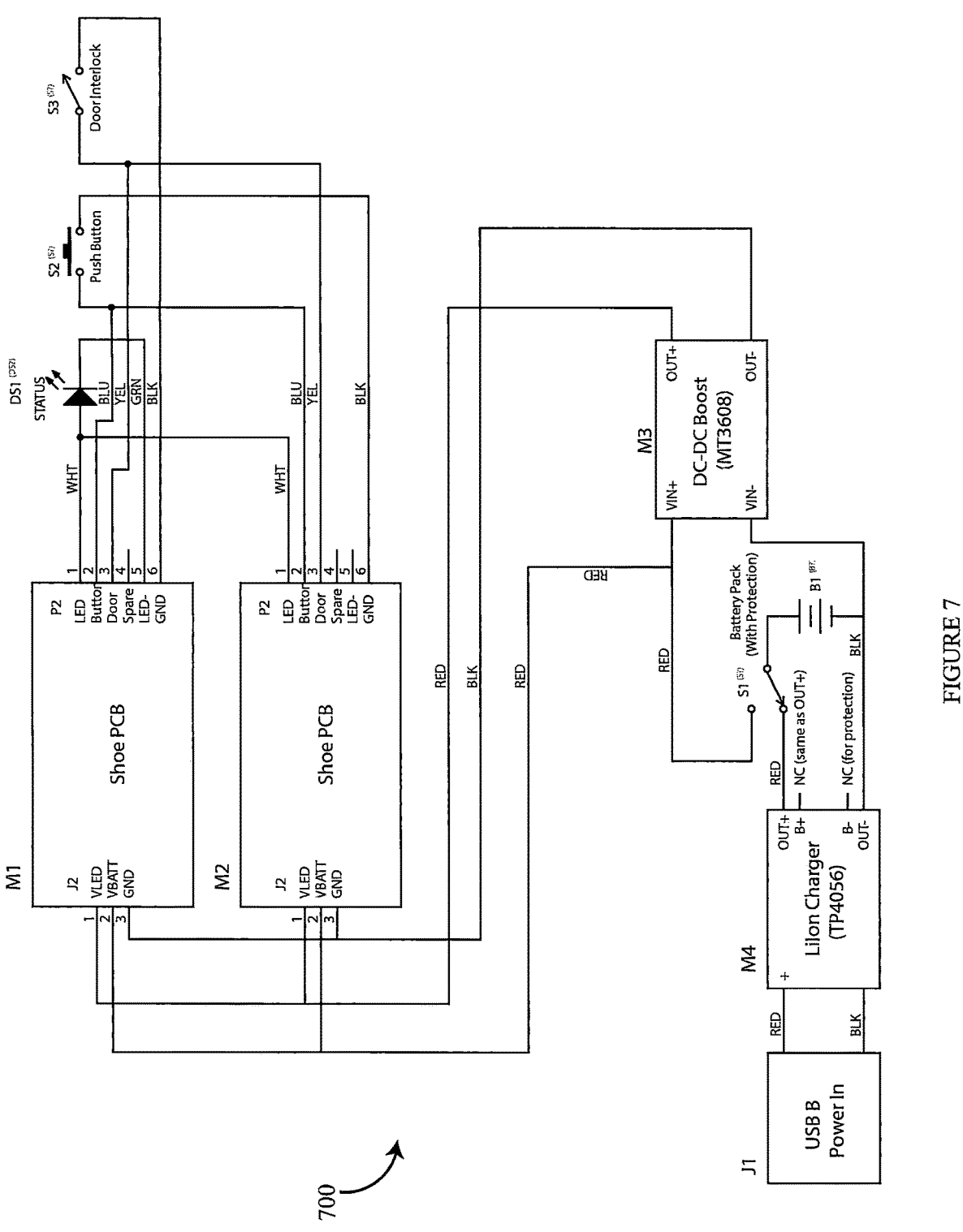
FIG. 7 depicts an alternate circuit wiring diagram for the UV-C shoe sole sanitizer chassis of FIG. 1.

FIG. 5 depicts UV-C controller circuitry 500 diagrams for operation of the shoe sole sanitizing device of FIG. 1. FIG. 6 depicts a circuit wiring 600 diagram for the UV-C shoe sole sanitizing device 100 chassis of FIG. 1. FIG. 7 depicts an alternate circuit wiring 700 diagram for the UV-C shoe sole sanitizing device 100 chassis of FIG. 1. All such chassis wiring 600/700 and controller circuitry 500 may be used consistent with embodiments of this disclosure.

FIG. 5 shows UV-C controller circuitry 500 for implementing operation of the sanitizer/sanitizing device 100 as described herein. As shown in FIG. 5, the circuitry 500 may include a processing unit and a memory unit. The memory unit may include a software module and a database. The software module includes instructions that, when executed by the processing unit, cause the processing unit to allow the user to sanitize shoes as disclosed herein. The database may comprise information about various parameters, standard UV-C light settings, and proximity sensor properties (e.g., range, speed, temperature limits, settings, dimensions, and weight), etc. While executing on the processing unit, the software or firmware module may perform processes for sanitize shoes including, for example, one or more operations included in a method described below with respect to FIGS. 5-10.

The software module may include various software and program modules to perform the various operations described herein. The software module and other programs can be embodied in computer-readable media containing instructions that, when executed by the processing unit, perform various operations such as those described herein. According to embodiments, the software module may be embodied in hardware, software, firmware, or any combination thereof.

Byway of example, and not limitation, computer-readable media may include any available computer storage media or communication media that can be accessed by the sanitizing device 100. Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Computer storage media includes volatile and non-volatile, removable and non-removable media implemented in any method or technology for storage of information such as computer-readable instructions, data structures, program modules, or other data. Computer storage media includes, but is not limited to, RAM, ROM, Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the sanitizing device 100. In the claims, the phrase "computer storage medium" and variations thereof do not include waves or signals per se and communication media.

The sanitizing device 100 may also include a user interface. The user interface allows the user to input information into the device or system 100 and view information.

The sanitizing device or system 100 may comprise any computer operating environment, such as hand-held devices, multiprocessor systems, microprocessor-based or programmable sender electronic devices, minicomputers, mainframe computers, and the like. Operation of the sanitizing device 100 may also be practiced in distributed computing environments where tasks are performed by remote processing devices. For example, the sanitizing device or system 100 may be a server that is accessed by using a web browser such as Internet Explorer® or Safari®. Furthermore, the device or system 100 may comprise a mobile terminal, such as a smart phone, a cellular telephone, a cellular telephone utilizing wireless application protocol (WAP), a personal digital assistant (PDA), an intelligent pager, a tablet computer such as the iPad®, a portable computer, a handheld computer, or a wireless fidelity (Wi-Fi) access point. The aforementioned systems and devices are examples, and the device or system 100 may comprise other systems or devices.

The UV-C controller circuitry 500 and circuit wiring 600 or 700 may control the operation of the sanitizing device 100 making it operative to sterilize, decontaminate or deactivate pathogens present on shoe 225 soles. The operation includes powering and controlling the portable, rechargeable battery-operated sanitizing device 100. The sanitizing device 100 components including: the housing enclosure 114 with the access door 110, the divider 200 within the housing enclosure 114 forming at least two shoe chambers 220, 220', multiple UV-C lights 330 located at the bottom of each shoe chamber, and proximity sensors 333 located among and in communication with the UV-C lights 330.

The controller circuitry 500 may operate the proximity sensors 333 to detect whether the shoe 225 sole is present near any of the proximity sensors 333. The sanitizing device 100 components further include a power source battery pack (See FIGS. 6 and 7) providing power to the device 100, including power to the UV-C lights 330 and the proximity sensors 333.

The controller circuitry 500 may further operate the device 100 to receive via the access door 110 and detect the pair of shoes 225 into the shoe chambers 220, 220' having one shoe per shoe chamber and once the access door 114 is closed activate a disinfection cycle for a predetermine amount of time, such a cycle may be initiated by a user pushing the disinfection cycle button 112.

Still further, the controller circuitry 500 may operate the device 100 to detect via the proximity sensors 333 which of the UV-C lights or lamps 330 has a shoe 225 sole directly atop it and then may only illuminate the UV-C lights 330 with a shoe sole directly atop for the predetermined amount of time. Not illuminating the UV-C lights 330 without a shoe sole atop helps prevent damage to the top of the shoes 225 by UV radiation unblocked by a shoe sole.

Figure 8:
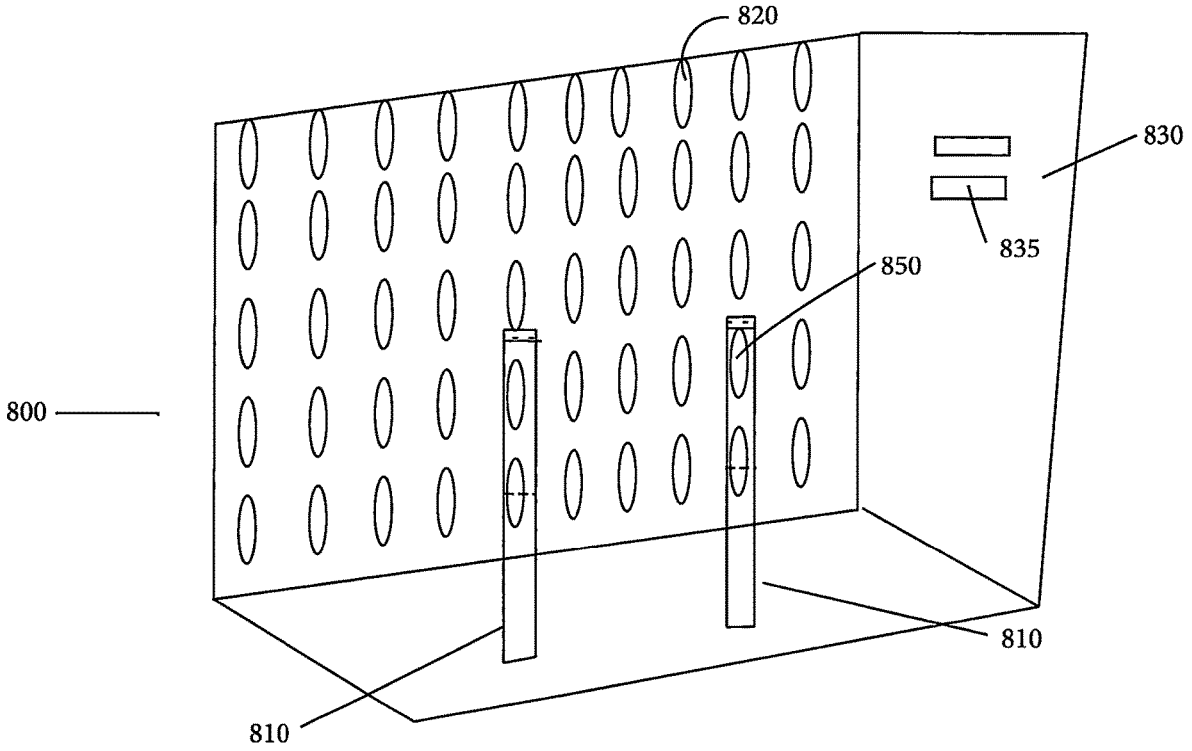
FIG. 8 depicts an internal perspective view of another embodiment of a UV-C shoe sole sanitizer having optional UV-C light shoe racks (or wand inserts) that disinfect and deodorize inner shoe surfaces and can be removed from the UV-C light circuit and attached to the sanitizer housing enclosure for convenience.

FIG. 8 depicts an internal perspective view of another embodiment of a rechargeable, battery-powered (not shown) UV-C shoe sole sanitizer 800 having optional UV-C light shoe racks (or wand inserts) 810 and 810' that disinfect and deodorize inner shoe surfaces and can be detachably removed from the UV-C shoe sole sanitizer 800 base and its associated UV-C light circuit and attached to the sanitizer 800 housing enclosure 830 for convenience. The sanitizer 800 also includes UV-C LED lamps 820 at its bottom base and UV-C LED lamps 850 within each wand insert 810 and 810'. The housing enclosure 830 may be completely enclose the shoe racks 810 and the UV-C LED lamps 820 with an access door and forming at least one shoe chamber as described with respect to FIG. 1.

Figure 9:
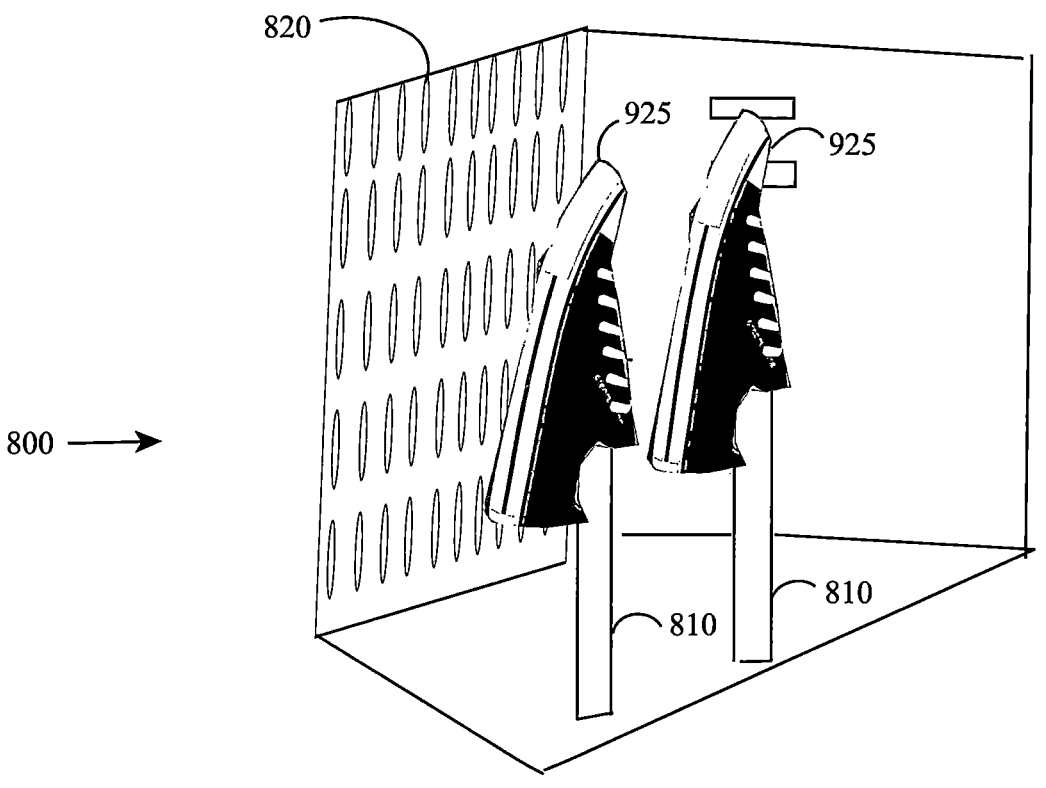
FIG. 9 depicts a perspective internal view of the UV-C shoe sanitizer of FIG. 8 with the optional shoe racks inserted in the shoes to disinfect and deodorize the internal shoe with the shoe soles facing and atop a UV-C LED light panel.

FIG. 9 depicts a perspective internal view of the UV-C shoe sanitizer 800 of FIG. 8 with the optional shoe racks 810 inserted into shoes 925 and 925' using UV-C LED lamps 850 to disinfect and deodorize the internal shoe with the shoe soles facing and atop UV-C LED lights 820.

Figure 10:
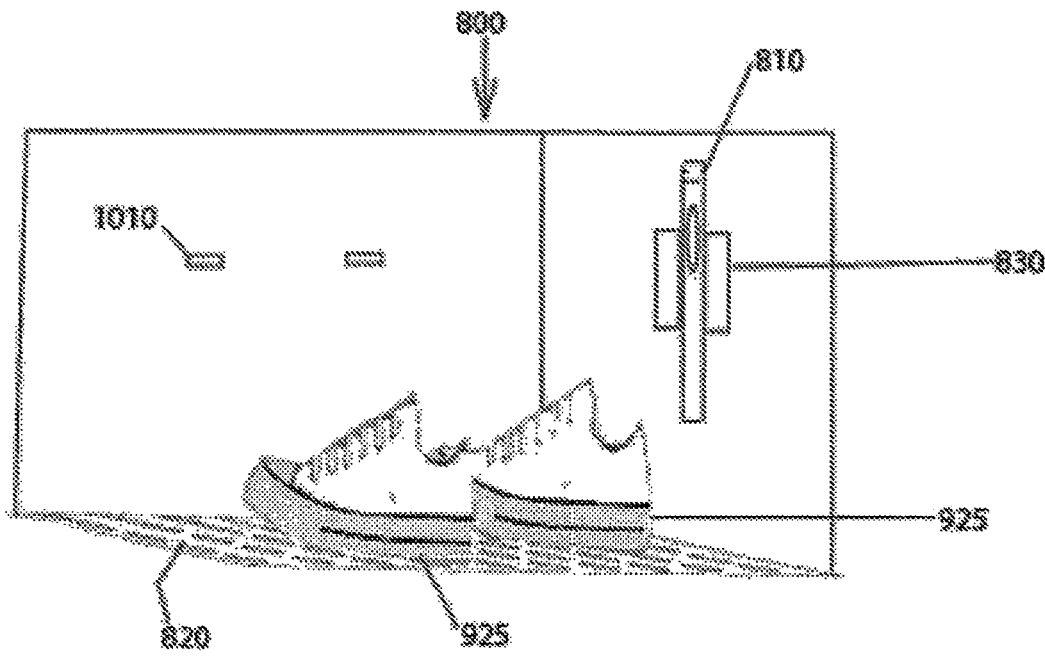
FIG. 10 depicts a perspective internal view of the placement of footwear atop the UV-C panel(s) with the sanitizing shoe racks removed from the sanitizer base circuit and attached to the internal side of the sanitizer housing enclosure.

FIG. 10 depicts a perspective internal view of the placement of shoes 925 directly atop the UV-C LED lights 820 panel(s) with the sanitizing shoe racks 810 removed from the sanitizer 800 base circuit and attached to the internal side of the sanitizer housing enclosure 830 at clamp 835. The wand inserts 810 may be detachably attached to the housing enclosure 830 at attachment points 1010. Each shoe wand 810 includes a UV-C light 850 in electrical communication with the control and battery power system via the attachment points 1010, both operative for insertion into a shoe to disinfect and deodorize inner portions of the shoe, at least one of the shoe wand inserts 810 present within each shoe chamber.

Although the subject matter presented herein has been described in language specific to computer structural features, methodological and transformative acts, specific computing machinery, and computer readable media, it is to be understood that the invention defined in the appended claims is not necessarily limited to the specific features, acts, or media described herein. Rather, the specific features, acts and mediums are disclosed as example forms of implementing the claims.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as example for embodiments of the disclosure.

What is claimed is:

1. A portable sanitizing device for decontaminating shoe soles, the device comprising:
   a housing enclosure, the housing enclosure including an access door wherein the shoe soles enter the housing enclosure via the access door when the access door is in an open position;
   a divider within the housing enclosure forming at least two shoe chambers, the divider in direct contact with the access door when the access door is in a closed position, wherein the divider, the housing enclosure, and the access door in the closed position isolates the at least two shoe chambers from one another and prevents any light to pass between the at least two shoe chambers;
   a plurality of UV-C light sources atop a panel at a bottom of each of the at least two shoe chambers, the plurality of UV-C light sources operative to direct light having UV-C wavelengths upward toward the access door when the access door is in the closed position;
   a plurality of proximity sensors located among and in communication with the plurality of UV-C light sources, the plurality of proximity sensors operative to detect whether a shoe sole is present near any of the plurality of proximity sensors; and
   an interlock in communication with the access door and in communication with the plurality of UV-C light sources, the interlock preventing illumination of at least a portion of the plurality of UV-C light sources when the access door is in an open position.

2. The portable sanitizing device of claim 1, wherein the plurality UV-C light sources comprise a plurality of UV-C LED light sources and the housing enclosure is completely without light from outside the housing enclosure when the access door is in the closed position.

3. The portable sanitizing device of claim 2, further comprising a timer operative to set the portable sanitizing device to decontaminate for a predetermined amount of time wherein when any of the plurality of proximity sensors detects the presence of a shoe sole near any of the plurality of proximity sensors, the portable sanitizing device exposes the shoe sole to at least a portion of the light for the predetermined amount of time set via the timer therein decontaminating the shoe sole exposed to at least the portion of the light.

4. The portable sanitizing device of claim 3, further comprising an indicator light wherein when the predetermined amount of time is complete, the portable sanitizing device indicates via the indicator light, completion of an active disinfection cycle of the portable sanitizing device.

5. The portable sanitizing device of claim 4, wherein the indicator light comprises a disinfection cycle indicator light in communication with the plurality of UV-C LED light sources wherein when the predetermined amount of time is complete the disinfection cycle indicator light turns off and wherein when the portable sanitizing device exposes the shoe sole to at least a portion of the light, the disinfection cycle indicator light turns on.

6. The portable sanitizing device of claim 2, further comprising a screen atop the plurality of UV-C LED light sources within each of the at least two shoe chambers wherein each screen is designated for placement of a shoe sole atop each screen.

7. The portable sanitizing device of claim 2, wherein the plurality of UV-C light sources are arranged among, between, and in communication with the plurality of proximity sensors from a heel end of the at least two shoe chambers to a toe end of the at least two shoe chambers; and wherein a controller having a processing unit and a memory unit including a software module having instructions that, when executed by the processing unit, cause the portable sanitizing device to detect, via the plurality of proximity sensors, which of the plurality UV-C LED light sources are covered by a shoe sole from the heel end of the at least two shoe chambers to the toe end of the at least two shoe chambers.

8. The portable sanitizing device of claim 7, wherein when at least one of the plurality of proximity sensors, is located in proximity to at least one of the plurality of UV-C LED light sources directly below the shoe sole, the controller is configured to cause the at least one of the plurality of proximity sensors to detect that the shoe sole is present atop the at least one of the plurality of UV-C LED light sources and configured to cause the at least one of the plurality of UV-C LED light sources to be illuminated.

9. The portable sanitizing device of claim 2, further comprising a battery and a battery recharging port for energizing the battery, the battery configured to power the portable sanitizing device including the plurality of UV-C LED light sources.

10. The portable sanitizing device of claim 1, wherein an inside of the housing enclosure is configured to prevent reflected light from irradiating any shoe top.

11. A method of deactivating pathogens present on shoe soles, the method comprising:

providing the portable, rechargeable battery-operated sanitizing device of claim 1 receiving via the access door a pair of shoes into the at least two shoe chambers where each shoe is inserted into one of the at least two shoe chambers;

once the access door is closed activating a disinfection cycle for a predetermine amount of time;

detecting via the plurality of proximity sensors which of the plurality of UV-C light sources has a shoe sole directly atop;

illuminating only the plurality of UV-C light sources with a shoe sole directly atop for the predetermined amount of time.

* * * * *